(12) United States Patent
Vekios et al.

(10) Patent No.: US 11,464,664 B2
(45) Date of Patent: Oct. 11, 2022

(54) UMBILICAL SPLINT AND METHOD OF USE

(71) Applicant: Roula Vekios, Kingston (CA)

(72) Inventors: Roula Vekios, Kingston (CA); Kimberly Meathrel, Wolfe Island (CA)

(73) Assignee: Roula Vekios, Kingston (CA)

( * ) Notice: Subject to any disclaimer, the term of this patent is extended or adjusted under 35 U.S.C. 154(b) by 425 days.

(21) Appl. No.: 16/787,861

(22) Filed: Feb. 11, 2020

(65) Prior Publication Data

US 2020/0170826 A1 Jun. 4, 2020

Related U.S. Application Data

(63) Continuation of application No. 15/003,323, filed on Jan. 21, 2016, now abandoned, which is a continuation of application No. 13/374,669, filed on Jan. 6, 2012, now abandoned.

(51) Int. Cl.
*A61F 5/30* (2006.01)
*A61B 17/00* (2006.01)
*A61B 17/08* (2006.01)

(52) U.S. Cl.
CPC ............ *A61F 5/30* (2013.01); *A61B 17/0057* (2013.01); *A61B 17/08* (2013.01); *A61B 2017/00637* (2013.01)

(58) Field of Classification Search
CPC ........ A61F 5/30; A61B 17/08; A61B 17/0057
See application file for complete search history.

(56) References Cited

U.S. PATENT DOCUMENTS

| 1,040,404 | A | | 10/1912 | Poindexter |
| 2,243,529 | A | | 5/1941 | Grossman et al. |
| 2,496,081 | A | | 1/1950 | Ambrose |
| 3,675,642 | A | | 7/1972 | Lord |
| 3,939,842 | A | * | 2/1976 | Harris ................... A61F 5/0093 607/113 |
| 4,241,912 | A | | 12/1980 | Mercer et al. |
| 4,263,914 | A | | 4/1981 | Pawlak |

(Continued)

FOREIGN PATENT DOCUMENTS

| FR | 954668 A | 4/1950 |
| GB | 23082 A | 11/1896 |

(Continued)

OTHER PUBLICATIONS

Extended European Search Report for EP 12864150.3 (dated Sep. 2, 2015).

*Primary Examiner* — Phong Son H Dang

(74) *Attorney, Agent, or Firm* — McAndrews Held & Malloy, Ltd.

(57) ABSTRACT

A use of an umbilical splint for shaping an umbilicus after an abdominal operation is described. The umbilical splint may comprise an insertion portion extending in a longitudinal direction and terminating at an insertion end for insertion into the umbilicus. Furthermore, the insertion portion may comprise a bulbous section near the insertion end. The bulbous section may be operable to apply pressure to a tissue of the umbilicus after the abdominal operation. The insertion portion may have different cross-sectional shapes including circular and oval. Finally, the insertion portion may be configured to engage the umbilicus such that the umbilical splint is retained within the umbilicus.

20 Claims, 13 Drawing Sheets

(56) References Cited

U.S. PATENT DOCUMENTS

| | | | |
|---|---|---|---|
| 4,583,542 A | | 4/1986 | Boyd |
| 4,693,236 A | | 9/1987 | Leprevost |
| D307,325 S | * | 4/1990 | Gardner, Jr. ................. D24/106 |
| 5,045,052 A | | 9/1991 | Sans |
| 5,817,124 A | | 10/1998 | Karell |
| 5,827,325 A | | 10/1998 | Landgrebe et al. |
| 5,924,423 A | | 7/1999 | Majlessi |
| 6,364,852 B1 | | 4/2002 | Lee |
| 6,589,193 B2 | | 7/2003 | Takashima |
| 6,752,818 B2 | | 6/2004 | Greene |
| D520,137 S | | 5/2006 | Melendez et al. |
| 7,211,059 B2 | | 5/2007 | Takashima |
| 7,875,267 B2 | | 1/2011 | Okajiwa et al. |
| D633,660 S | * | 3/2011 | Cooke .......................... D30/156 |
| D636,484 S | * | 4/2011 | Tiemens ................. A61F 11/08 D24/106 |
| 8,646,458 B2 | * | 2/2014 | Bernard ............. A61F 9/00772 128/887 |
| D706,941 S | * | 6/2014 | Vekios ......................... D24/190 |
| 9,615,953 B2 | * | 4/2017 | Blurton ................. A61B 17/42 |
| 2002/0147457 A1 | * | 10/2002 | Rousseau ............. A61F 2/0063 623/23.72 |
| 2006/0058576 A1 | * | 3/2006 | Davies ................... A61F 5/445 600/32 |
| 2007/0255307 A1 | | 11/2007 | Cummings, III |
| 2009/0138015 A1 | * | 5/2009 | Conner ................. A61F 2/4684 606/90 |
| 2009/0157140 A1 | * | 6/2009 | Martino ............. A61N 1/36007 604/332 |
| 2009/0216071 A1 | * | 8/2009 | Zipper ..................... A61F 6/08 128/834 |
| 2009/0275795 A1 | * | 11/2009 | Martino .................. A61F 5/445 600/32 |
| 2010/0121291 A1 | * | 5/2010 | Davies .................... A61F 5/441 604/333 |
| 2010/0298646 A1 | | 11/2010 | Stellon |
| 2011/0125185 A1 | | 5/2011 | Stopek et al. |
| 2012/0324949 A1 | | 12/2012 | Bettis |
| 2014/0000628 A1 | * | 1/2014 | Avery, Jr. .......... A61F 13/55175 53/461 |

FOREIGN PATENT DOCUMENTS

| | | |
|---|---|---|
| JP | 2007126173 A | 5/2007 |
| JP | 2009148461 A | 9/2009 |
| JP | 2009148462 | 9/2009 |
| JP | 2009149580 | 9/2009 |
| JP | 2009149581 | 9/2009 |

\* cited by examiner

UMBILICAL SPLINT AND METHOD OF USE

RELATED APPLICATIONS

This application is a continuation of U.S. patent application Ser. No. 15/003,323, filed Jan. 21, 2016, which is continuation of U.S. patent application Ser. No. 13/374,669, filed Jan. 6, 2012, both of which are hereby incorporated by reference in their entirety.

FIELD OF THE INVENTION

This invention relates to an umbilical splint, and more particularly towards an umbilical splint for post-operative care and methods of use.

BACKGROUND OF THE INVENTION

During certain types of abdominal surgery, incisions are made in the umbilicus or the surrounding umbilical (belly button) region. Examples of such procedures include abdominoplasty (i.e. tummy tuck), panniculectomy, Transverse Rectus Abdominis Myocutaneous (TRAM) flap procedures, endoscopic surgeries, and the like. Circumferential umbilical incisions can lead to contracture and closure of the umbilicus or umbilical opening due to the physiological forces of scar contracture. This can lead to deformities of the umbilicus, as well as infections.

Deformity of the umbilicus can also occur after pregnancy, especially if a caesarean section is required, and after weight loss.

Current products used to counteract the forces of scar contracture following umbilical or other abdominal surgery include using a marble or a foam earplug. However, marbles are difficult to keep in place and may be difficult to ensure sterility. Furthermore, foam earplugs are not stiff enough to counteract the forces of scar contracture and can lead to infection due to its porous nature.

Accordingly, there is a need for a device and method to counteract the forces of scar contracture within the umbilicus and to reduce the risk of infection after abdominal surgery.

SUMMARY OF THE INVENTION

Accordingly, it is an object of this invention to at least partially overcome some of the disadvantages of the prior art.

The present invention is directed to an umbilical splint for post-operative care. For example, the umbilical splint may be used post-abdominoplasty or after other cosmetic procedures. Similarly, the umbilical splint may be used after an endoscopic, abdominal or laparoscopic surgery or after a hernia repair. The umbilical splint may also be used as a paediatric device, such as, for example, for children recovering from congenital abdominal repair. In some instances, the umbilical splint may also be used to transform a protruding umbilicus (i.e. "an outie") into a depression (i.e. "an innie"). In general, the present invention may be used to avoid stenosis of the belly button. Other uses within the umbilicus may also be possible.

The umbilical splint is designed to be inserted into the umbilicus at the time of surgery to counteract the forces of scar contracture. In this way, in at least one embodiment, the umbilical splint may be configured to decrease stenosis of the umbilicus following surgery.

The umbilical splint may be configured to prevent cosmetic deformities and late infections at the site. In post-partum women, the splint may be inserted immediately post-partum to help shape the umbilicus during retraction of the distended pregnant abdomen. Once inserted, the umbilical splint may be worn periodically or continuously, except for personal hygiene purposes, to aid in the healing process. In some embodiments, the umbilical splint may be maintained within the umbilicus for a pre-determined period of time.

The shape of the umbilical splint is designed to promote the healing of the umbilicus and to reduce scarring by applying constant pressure to the entire umbilical region. In surgical patients where a scar is present, a silicone gel sheet may be applied to the splint following suture removal to improve the overall cosmesis (i.e. physical appearance) of the scar. Past research has shown that application of silicone to scars, as well as the application of pressure, improves the overall cosmesis of the mature scar.

The umbilical splint may be configured to have several advantages, such as, resist the forces of scar contracture to maintain an aesthetically pleasing shape and size of the umbilicus, apply pressure to the surrounding scar tissue, and apply silicone gel sheeting in combination with the applied pressure to promote healing. Furthermore, a slow-release antibiotic covering or medicament may be used to decrease the chances of wound infection.

The overall form of the umbilical splint is designed both to improve the shape of the umbilicus and to retain the splint within the umbilicus. Accordingly, the umbilical splint may be configured with a bulbous section with a pre-determined shape. The bottom bulbous portion may be manufactured out of hard plastic. However, it should be understood that other materials may be used, such as glass, metal, medical ceramic, silicone, medical plastics, minerals, and the like. Furthermore, in some embodiments, the umbilical splint may have a rigid core surrounded by a softer more flexible outer material for improved comfort. For example, the outer material may be a soft, flexible plastic or an alternative material such as medical grade silicone, and the like.

The bulbous section may be configured to provide an idealized shape for the umbilicus to conform to. Furthermore, the bulbous section may stretch or otherwise provide pressure to the umbilicus to resist the forces of scar contracture. In some embodiments, the shape of the bulbous section may be symmetric. A symmetric bulbous section may provide even, constant pressure to the umbilical tissue. Furthermore, in some embodiments, the cross-section of the bulbous section or the entire insertion portion may be selected for aesthetic purposes and may be symmetric or asymmetric. The cross-sectional shape of the bulbous section provided in the preferred embodiments should not be construed as limiting.

To retain the umbilical splint within the umbilicus, the umbilical splint may have a retaining section located adjacent the bulbous section. The retaining section and the bulbous section may form the insertion portion of the umbilical splint. The bulbous section of the insertion portion may be between an insertion end of the insertion portion and the retaining section.

The retaining section may be configured to engage the umbilicus so as to retain the umbilical splint within the umbilicus. For example, the retainment section may engage an umbilical lip of the umbilicus near the umbilical opening, with the bulbous section being inserted further into the umbilicus to apply pressure to the tissue inside the umbilicus.

The shape of the bulbous section may also help to retain the umbilical splint within the umbilicus. In some embodiments, a bulbous section with an asymmetric shape may be better at being retained within the umbilicus or may provide an advantageous distribution of pressure to the surrounding tissue. Finally, in some embodiments, an adhesive may be used or a further mechanism, such as a tape or a bandage, may be placed over the umbilical splint and against the abdominal wall in order to retain the umbilical splint within the umbilicus.

In some embodiments, the umbilical splint may have an external flange for covering the umbilical opening, protecting against dust and pathogens entering the umbilical opening. The external flange may also apply direct pressure to the external circumferential umbilical scar. In this manner, the external flange may reduce the formation and/or the appearance of scars. Furthermore, the external flange may help retain any medicament placed inside the umbilicus prior to the insertion of the umbilical splint.

The external flange may be manufactured out of a rigid material; for example, the same hard plastic as the rest of the umbilical splint. In such embodiments, the umbilical splint may be formed as a single piece. Alternatively, the protective lip may be manufactured out of a softer plastic or a flexible material. A flexible external flange may be operable to bend and move with the abdominal wall when inserted into the umbilical cavity.

In one aspect, the present invention resides in a use of an umbilical splint for shaping an umbilicus after an abdominal operation. The umbilical splint may comprise an insertion portion extending in a longitudinal direction and terminating at an insertion end for insertion into the umbilicus. Furthermore, the insertion portion may comprise a bulbous section near the insertion end. The bulbous section may be operable to apply pressure to a tissue of the umbilicus after the abdominal operation. Finally, the insertion portion may be configured to engage the umbilicus such that the umbilical splint is retained within the umbilicus.

In another aspect, the present invention resides in an umbilical splint. The umbilical splint may include an insertion portion extending in a longitudinal direction and terminating at a insertion end for insertion into an umbilicus. The insertion portion may include a bulbous section having a bulbous circumference, the bulbous section near the insertion end; a retaining section having a retaining circumference less than the bulbous circumference; and an external flange coupled to the insertion portion. The bulbous section may be disposed between the retaining section and the insertion end. The external flange may include an underside surface facing the insertion end of the insertion portion, and an exterior surface, opposite the underside surface. In a preferred embodiment, a ratio of the bulbous circumference to the retaining circumference may be between 1.0 and 1.4. In a more preferred embodiment, the ratio of the bulbous circumference to the retaining circumference may be between 1.1 and 1.2.

In yet another aspect, the present invention resides in a method of post-operative care. The method may include inserting an umbilical splint into an umbilicus after an abdominal operation, the umbilical splint comprising an insertion portion extending in a longitudinal direction and terminating at an insertion end; retaining the umbilical splint within the umbilicus using a retaining section of the insertion portion to engage the umbilicus; applying pressure to the umbilicus using a bulbous section of the insertion portion to shape the umbilicus after the abdominal operation; and maintaining the umbilical splint within the umbilicus for a period of time until the umbilicus has healed from the abdominal operation.

Further and other features of the invention will be apparent to those skilled in the art from the following detailed description of the embodiments thereof.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Figure 1:
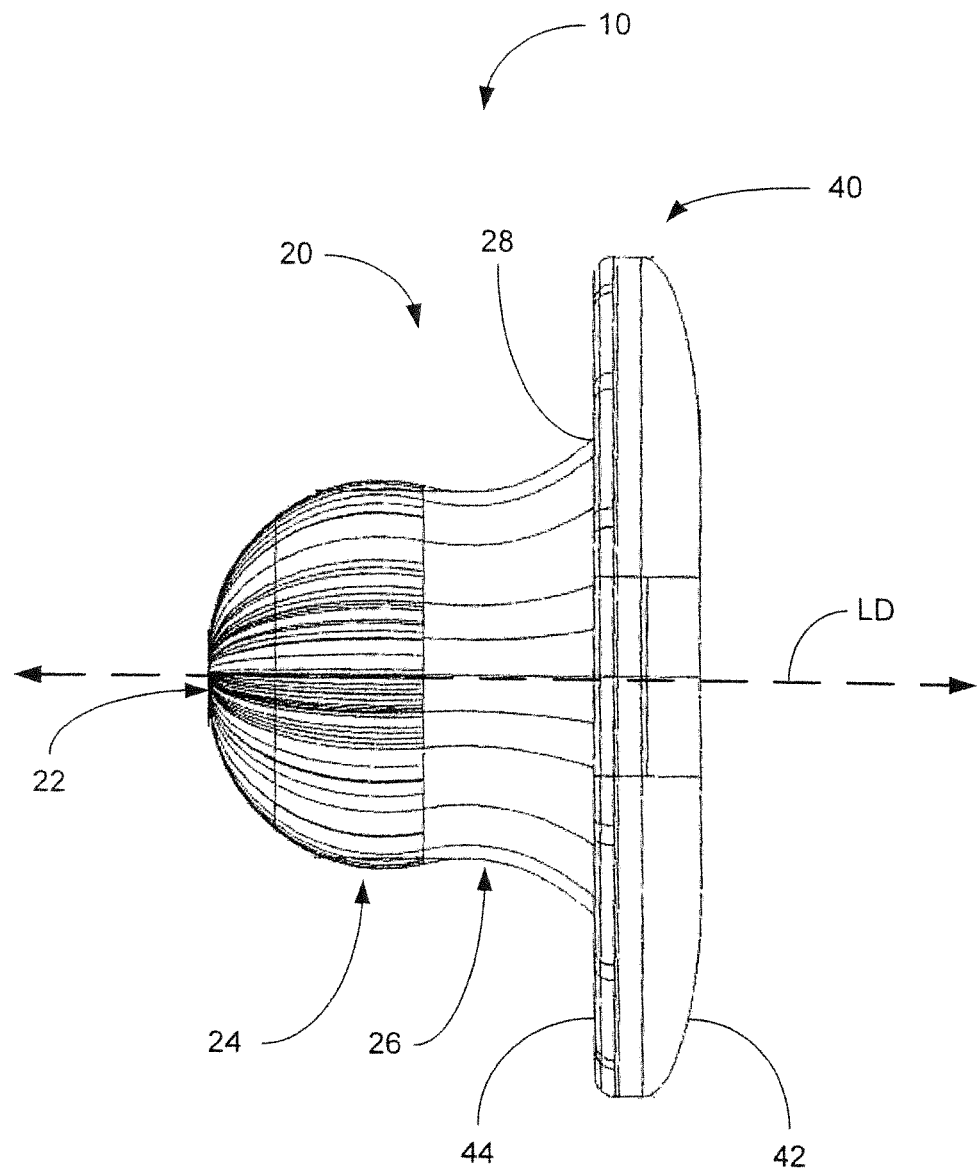
FIG. 1 shows a side profile view of an umbilical splint in accordance with an embodiment of the present invention.

Referring now to FIG. 1, an umbilical splint 10 is shown in accordance with an embodiment of the present invention.

The umbilical splint 10 is configured with an insertion portion 20 terminating at an insertion end 22 and an external flange 40.

The insertion portion 20 extends in a longitudinal direction LD, shown in dashed lines, for insertion into an umbilicus. The insertion portion 20 includes an insertion end 22, a bulbous section 24 and a retaining section 26. The bulbous section 24 is disposed between the insertion end 22 and the retaining section 26.

The umbilical splint 10 may also include an external flange 40. The external flange 40 is configured with an external surface 42 and an underside surface 44. The underside surface 44 of the external flange 40 faces the insertion end 22 of the insertion portion 20. The insertion portion 20 and the external flange 40 may be joined at an intersection 28.

Figure 2A:
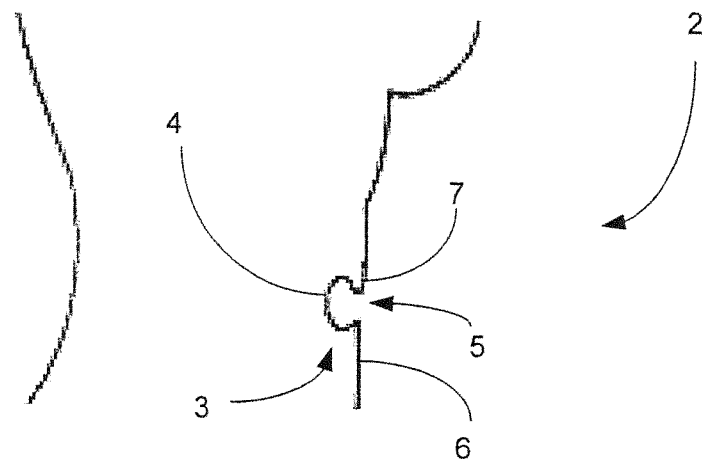
FIG. 2A shows a patient with the various parts of the umbilicus in accordance with an embodiment of the present invention.

As seen in FIG. 2A, a patient 2 has an umbilicus 3 (i.e. a belly button or navel). As described herein, the umbilicus 3 includes umbilical tissue 4 interior to the umbilical opening 5. The umbilicus 3 is surrounded by abdominal tissue 6 surrounding the umbilical opening 5. Furthermore, the umbilical opening 5 may include a lip 7. The lip 7 may consist of abdominal tissue 6, such as for example, the epidermis or skin.

Figure 2B:
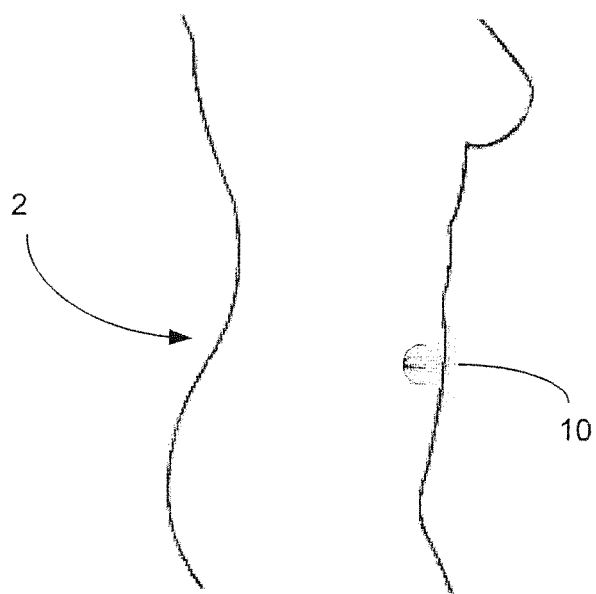
FIG. 2B shows a side view of a patient with an umbilical splint inserted into the umbilicus in accordance with an embodiment of the present invention.

Referring now to FIG. 2B, the umbilical splint 10 is inserted into the patient 2 by placing the insertion end 22 of the umbilical splint 10 into the umbilicus 3. The bulbous section 24 is operable to apply pressure to the umbilical tissue 4. The shape of the bulbous section 24 is configured to stretch or otherwise provide pressure to the umbilical tissue 4 of the umbilicus 3 to resist the forces of scar contracture. Furthermore, in some embodiments, the insertion portion 20 is designed to engage the umbilicus 3 such that the umbilical splint 10 is retained within umbilicus 3 without additional aid.

Upon insertion into the umbilicus 3, the retaining section 26 may be configured to be disposed at a level even with the umbilical opening 5. The retaining section 26 may be configured to engage a lip 7 of the umbilicus 3. In some embodiments, the retaining section 26 may interact with the lip 7 at the umbilical opening 5 to keep the umbilical splint 10 within the umbilicus 3.

In another preferred embodiment, when the insertion portion 20 of the umbilical splint 10 is inserted into the umbilicus 3, the external flange 40 covers the umbilical opening 5. Furthermore, the external flange 40 may extend beyond the umbilical opening 5 over the abdominal tissue 6 surrounding the umbilical opening 5. The underside surface 44 of the external flange 40 may lie against the abdominal tissue 6 surrounding the umbilical opening 5 and may protect the umbilicus 3 from outside moisture and debris. Similarly, if a medicament is used in combination with the umbilical splint 10, the external flange 40 may be operable to contain the medicament within the umbilicus 3.

Figure 3:
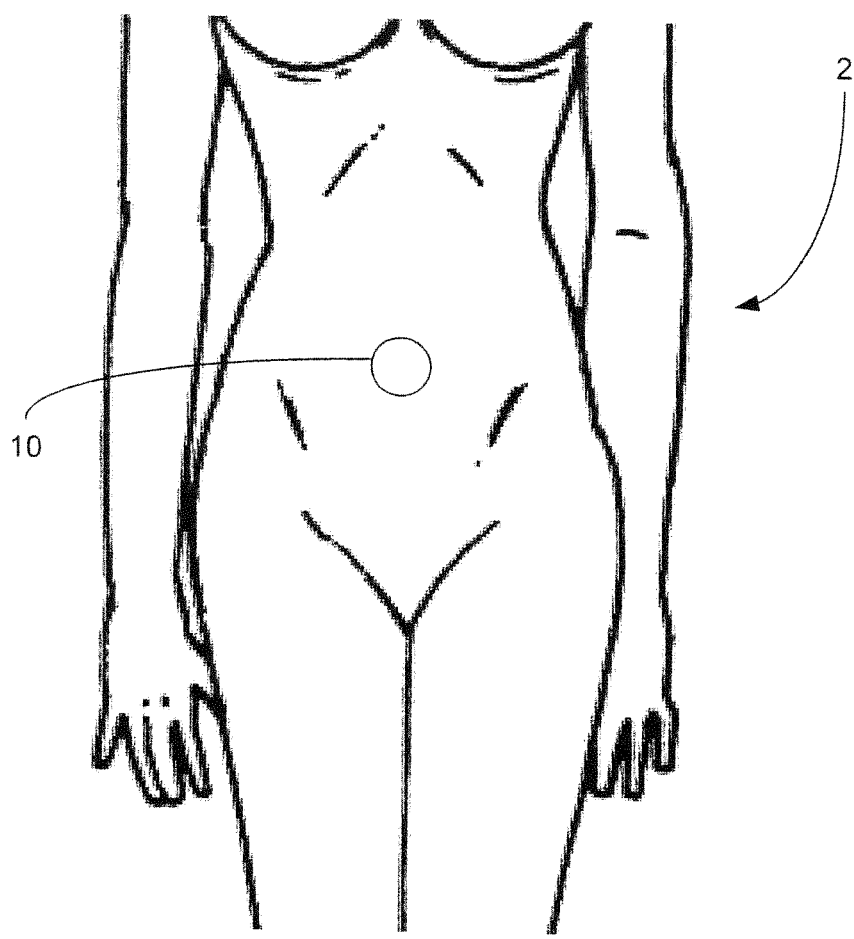
FIG. 3 shows a frontal view of a patient with an umbilical splint inserted into the umbilicus in accordance with an embodiment of the present invention.

Referring now to FIG. 3, a front profile of a patient 2 is shown with an umbilical splint 10 inserted into the umbilicus 3. As illustrated, only the exterior surface 42 of the external flange 40 is visible, once the umbilical splint 10 is inserted into the umbilicus 3.

To retain the umbilical splint 10 within the umbilicus 3, the umbilical splint 10 is configured to utilize the forces applied to the components of the insertion portion 20 to maintain contact between the umbilical splint 10 and the patient 2. In a preferred use, a force (not shown) is exerted by the umbilical tissue 4 of the patient 2 against the bulbous section 24 of the insertion portion 20 to hold the umbilical splint 10 in place. For example, in some embodiments, enough friction and pressure may be generated by the umbilical tissue 4 against the bulbous section 24 to maintain the insertion portion 20 within the umbilicus 3.

In another preferred use, a different force (not shown) may be exerted against the retaining section 26 to impede any longitudinal force acting to withdraw or expunge the umbilical splint 10 from the umbilicus 3. For example, the lip 7 of the umbilical opening 5 may exert a force or pressure against the retaining section 26, holding the insertion portion 20 in place within the umbilicus 3. In this manner, the retaining section 26 is configured to aid in positioning the umbilical splint 10 within the umbilicus 3. Furthermore, the combination of pressure and friction from the umbilical tissue 4 and lip 7 acting on the bulbous section 24 and retaining section 26, respectively, may cooperatively retain the umbilical splint 10 within the umbilicus 3 without any external aid.

In alternate embodiments, additional retaining means may also be utilized. For example, tape or any other adhesive (not shown) may be used to keep the umbilical splint 10 within the umbilicus 3. Furthermore, a bandage or any other wrapping device may be used to wrap the umbilical splint 10 against the abdominal tissue 6 of the patient 2, keeping the umbilical splint 10 in place.

Referring now to FIG. 4A-FIG. 4D, umbilical splints 10A, 10B, 10C and 10D (hereinafter referred to collectively as umbilical splints 10) are illustrated in different preferred embodiments. As different patients 2 may have differently sized and/or shaped umbilici, the umbilical splint 10 may also be configured for different sizes and/or shapes. Furthermore, a patient 2 may desire a differently shaped umbilicus 3 than another patient 2. Accordingly, the appropriate umbilical splint 10 for a given patient 2 may be dependent on a preferred outcome of what the healed umbilicus 3 should look like. Values may be dependent on the starting size of the umbilicus 3 post-surgery, prior to weight loss or subsequent to pregnancy. Furthermore, the umbilical splint 10 used may be dependent on the desired aesthetic. Other values for the different measurements listed may be used in alternate embodiments. The provided values described in the preferred embodiments should not be construed as limiting.

Referring briefly to FIG. 1, the umbilical splint 10 includes an insertion portion 20 having a bulbous section 24, a retaining section 26 and an intersection 28 of the insertion portion 20 and the external flange 40. Referring now to FIG. 4A to FIG. 4D in view of FIG. 1, the bulbous section 24 is defined by a bulbous circumference. As the umbilical splint 10A, 10B, 10C, 10D are shown as substantially circular in the preferred embodiments; the bulbous circumference of the bulbous section 24 in the preferred embodiments is defined by a bulbous diameter 30 and equation (1):

$$\text{Circumference} = \pi \times \text{Diameter} \quad (1)$$

Similarly, a retaining circumference of the retaining section 26 of the umbilical splint 10A, 10B, 10C, 10D may be defined by a retaining diameter 32 and equation (1). Finally, an opening circumference may be defined by an opening diameter 34 at the intersection 28 of the insertion portion 20 and the external flange 40 and equation (1). The opening circumference may be substantially related to the size of the umbilical opening 5.

As seen in FIGS. 1 to 5, the bulbous circumference, retaining circumference and opening circumference may lay in one or more planes normal to the longitudinal direction LD. In a preferred embodiment, the bulbous, retaining and opening circumferences are parallel to one another. Furthermore, although the term circumference has been used, it should be understood that the cross-sectional shape of the insertion portion 20 and/or bulbous section 24, retaining section 26 and intersection 28 of the umbilical splint 10 is not limited to a circular shape. In other embodiments, the perimeter or cross-sectional shape may be ovular (as shown in FIGS. 7A to 7D and 8A to 8D, for example) or asymmetric, rather than a circular circumference. Accordingly, the circular cross-section of the insertion portion 20, as illustrated in FIGS. 1 to 5, should not be construed as limiting.

The insertion portion 20 of the umbilical splint 10 may also be defined by an insertion length 36 in the longitudinal direction LD. This is the length of the umbilical splint 10 that is inserted into the patient 2. Although dependent on a particular patient 2, the insertion length 36 may be closely associated with the other values, shapes and/or sizes of the insertion portion 20 of the different umbilical splints 10.

The external flange 40 of the umbilical splint 10 may not be patient dependent. The external flange 40 must be large enough to extend beyond the umbilical opening 5; however, the external flange 40 is not inserted into the umbilicus 3 and therefore, the external flange 40 of the umbilical splint 10 may take a standard size and/or shape, as shown in FIG. 4A through FIG. 4D. Similarly, as the exterior surface 42 of the eternal flange 40 is not inserted into the umbilicus 3, it may take on any suitable form to satisfy the aesthetic preference of the patient 2. Different shapes, sizes, patterns, textures and the like, may be used on the external surface 42 of the external flange 40.

In FIG. 4A-FIG. 4D in view of FIG. 1, the external flange 40 includes a flange circumference, defined by a flange diameter 46, and a flange length 48. As the external flange 40 is not inserted into the umbilicus 3, the external flange in each of FIG. 4A-FIG. 4D is standard with a flange diameter of 21.00 mm and a flange length of 2.71 mm. These values should not be construed as limiting as other values are possible in various embodiments.

Table 1 provides a listing of the different values for the preferred embodiments of the umbilical splint 10A, 10B, 10C, 10D illustrated in FIG. 4A to FIG. 4D.

TABLE 1

Measured Values of the Preferred Embodiments

| (in mm) | Umbilical Splint 10A (FIG. 4A) | Umbilical Splint 10B (FIG. 4B) | Umbilical Splint 10C (FIG. 4C) | Umbilical Splint 10D (FIG. 4D) |
| --- | --- | --- | --- | --- |
| Bulbous Circ. | 8.04 π | 10.00 π | 12.00 π | 14.00 π |
| Retainer Circ. | 7.22 π | 9.21 π | 11.91 π | 12.69 π |
| Opening Circ. | 10.00 π | 12.00 π | 14.00 π | 14.00 π |
| Insertion Length | 8.07 | 10.00 | 12.00 | 12.00 |
| Flange Circ. | 21.00 π | 21.00 π | 21.00 π | 21.00 π |
| Flange Length | 2.71 | 2.71 | 2.71 | 2.71 |

Figure 4A:
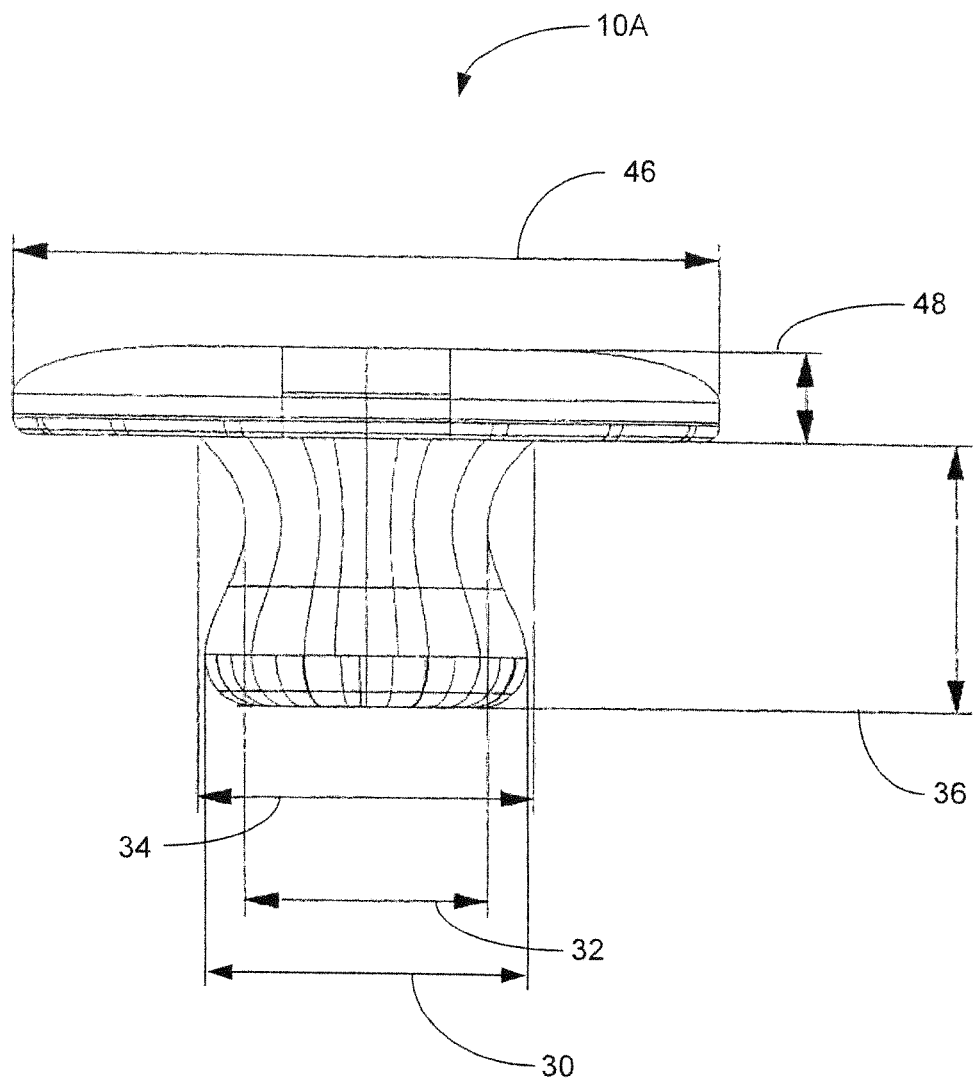
FIG. 4A shows a side profile view of an umbilical splint in accordance with a preferred embodiment of the present invention.
Figure 4B:
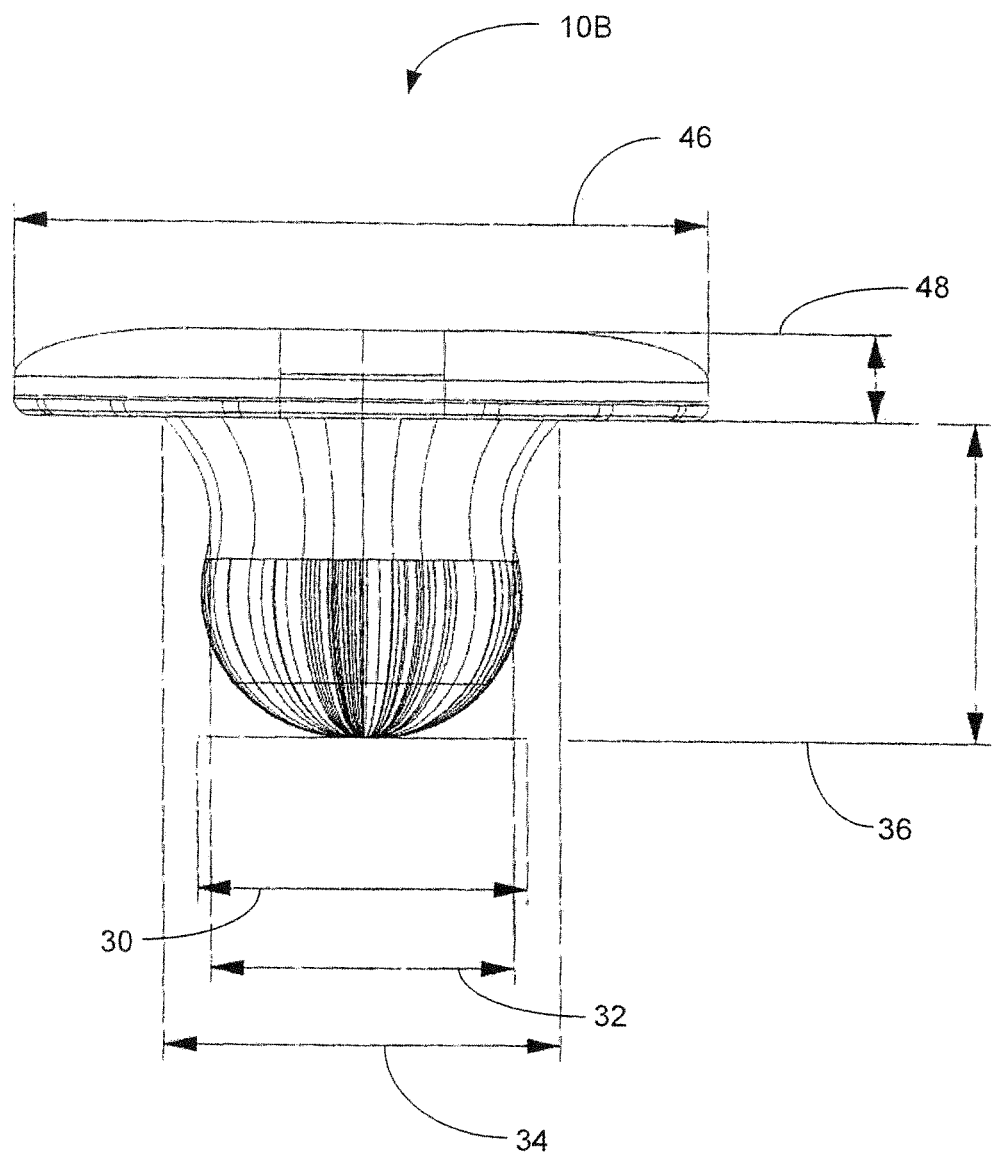
FIG. 4B shows a side profile view of an umbilical splint in accordance with a second preferred embodiment of the present invention.
Figure 4C:
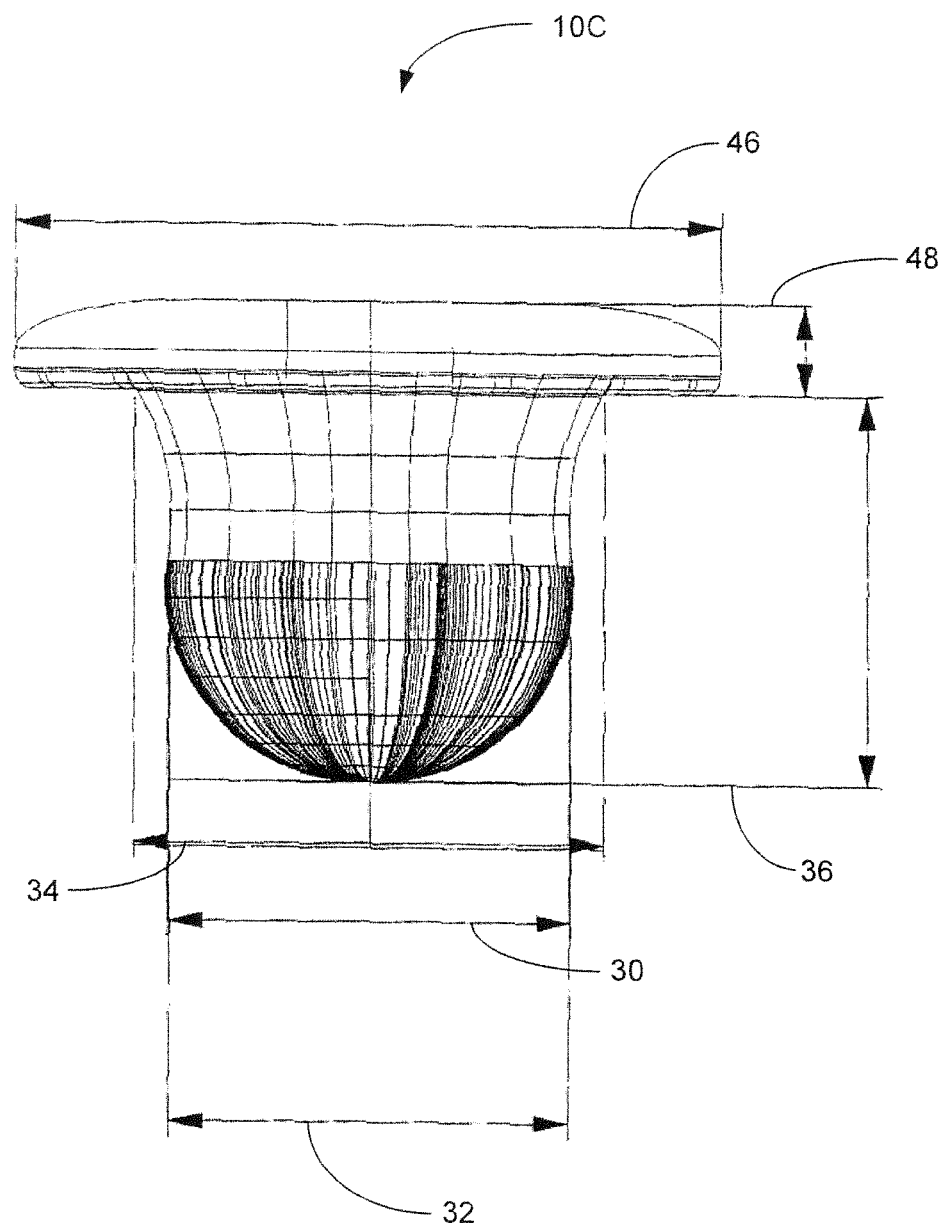
FIG. 4C shows a side profile view of an umbilical splint in accordance with a third preferred embodiment of the present invention.
Figure 4D:
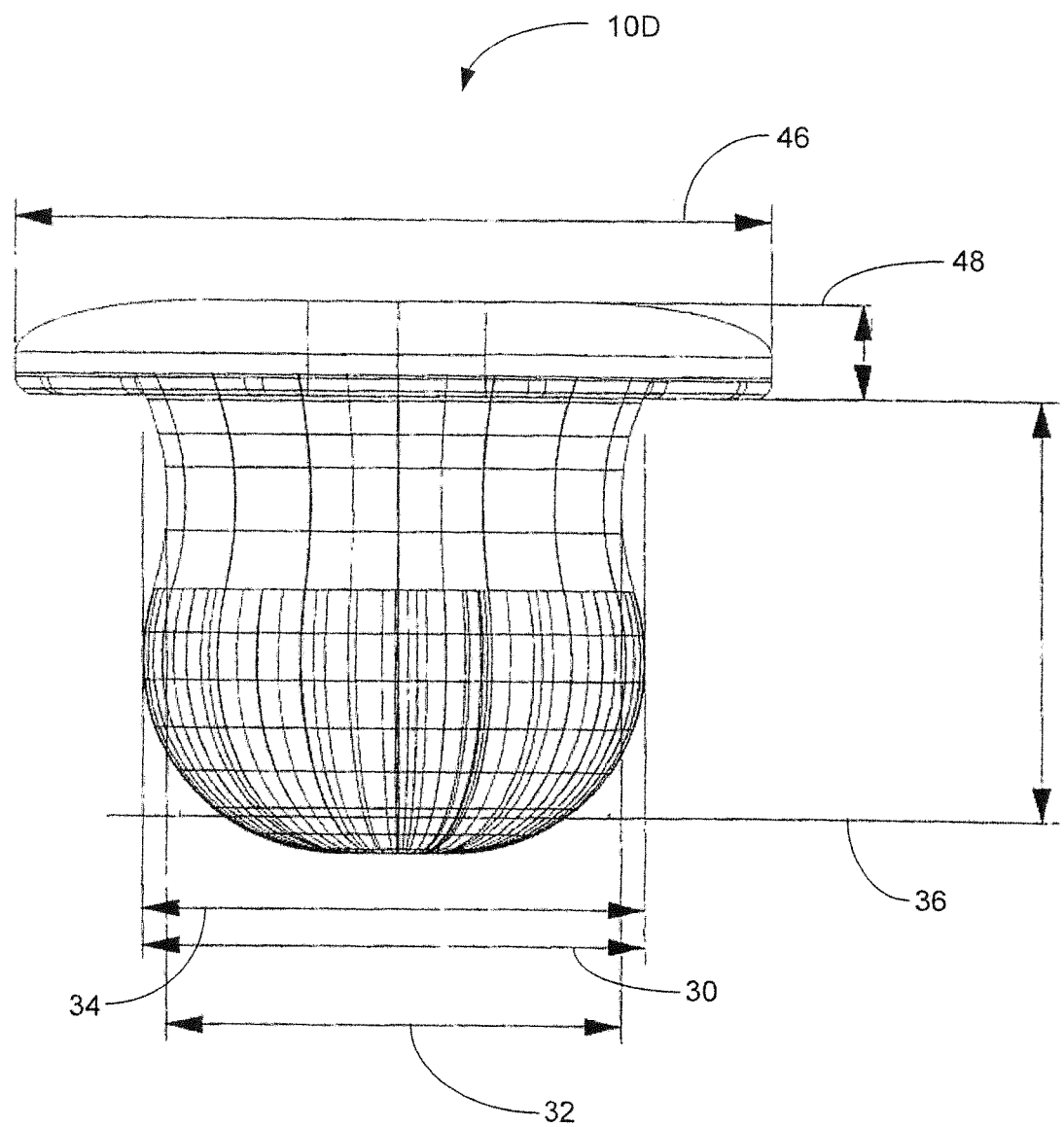
FIG. 4D shows a side profile view of an umbilical splint in accordance with a fourth preferred embodiment of the present invention.

In seen in FIG. 4A, the insertion end 22 is substantially planar. A planar insertion end 22 (i.e. a flat bottom) may be desirable for some patients. In other embodiments, as illustrated in FIG. 4B-FIG. 4D, the insertion end 22 may be rounded.

As also seen in FIG. 4A-FIG. 4D, particular ratios between the bulbous circumference and retaining circumference have been discovered to be particularly advantageous. The ratios may be based upon the bulbous diameter 30 and the retaining diameter 32. Table 2 provides a listing of the bulbous circumference to retaining circumference described in the preferred embodiments illustrated in FIG. 4A-FIG. 4D:

TABLE 2

Calculating Bulbous Circ. to Retaining Circ. Ratios

| (in mm) | Bulbous Diameter 30 | Retaining Diameter 32 | Ratio |
| --- | --- | --- | --- |
| 10A (FIG. 4A) | 8.04 | 7.22 | 1.11 |
| 10B (FIG. 4B) | 10.00 | 9.21 | 1.09 |
| 10C (FIG. 4C) | 12.00 | 11.91 | 1.01 |
| 10D (FIG. 4D) | 14.00 | 12.69 | 1.10 |

Although the above ratios are described with respect to preferred embodiments, it should be understood that additional ratios relating the bulbous circumference to the retaining circumference are also possible. For example, in some embodiments a ratio of 1.2 to 1.4 may be particularly desirable.

Figure 5:
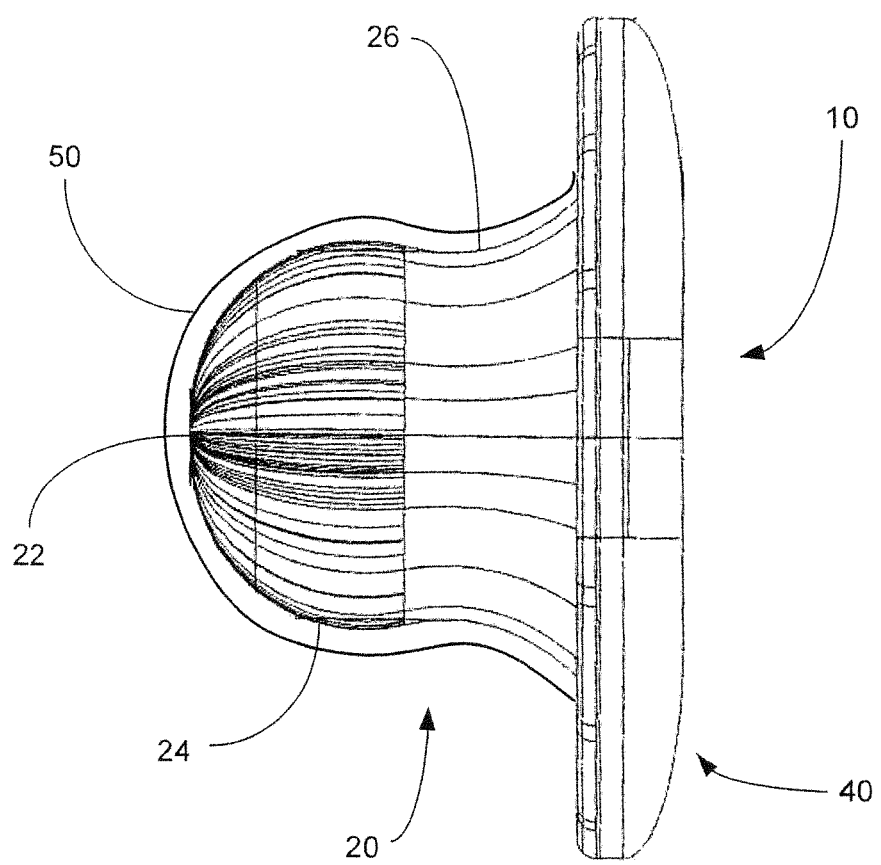
FIG. 5 shows a side profile view of an umbilical splint having an application layer in accordance with an embodiment of the present invention.

Referring now to FIG. 5, an application layer 50 is applied to the insertion portion 20 of the umbilical splint 10. For example, the application layer 50 may include a medicament or a silicone gel sheet. For example, an antibiotic may be used to reduce the chances of infection. Furthermore, other forms of silicone than silicone gel sheets may be added. The external flange 40 of the umbilical splint 10 is then operable to contain the medicament within the umbilicus 3 when laid securely against the abdominal tissue 6 surrounding the umbilical opening 5.

If the application layer 50 comprises a silicone gel sheet, the silicone gel sheet is used to reduce the effects of scarring. The inventors have appreciated that the umbilical splint 10 is ideal for providing constant pressure to the umbilical tissue 4. This pressure may also be used to apply silicone against the umbilical tissue 4 of the umbilicus 3 to promote healing and improve the overall cosmesis of the area. When placed on the exterior of the insertion portion 20, the application layer 50 comprising a silicone gel sheet is operable to be pressed up against the walls of the umbilicus 3 for as long as the umbilical splint 10 is retained within the umbilicus 3. As silicone is known to reduce the appearance of scarring, the umbilical splint can combine both pressure and silicone against the umbilical tissue 4 to aid in the healing of the umbilicus 3, for example, after an abdominal operation.

Although the application layer 50 in FIG. 5 is shown surrounding the entire insertion portion 20, it should be understood that a more localized application layer 50 may also be used. For example, the application layer 50 may surround the insertion end 22 and/or bulbous section 24 only, without extending over the retaining section 26.

Figure 6:
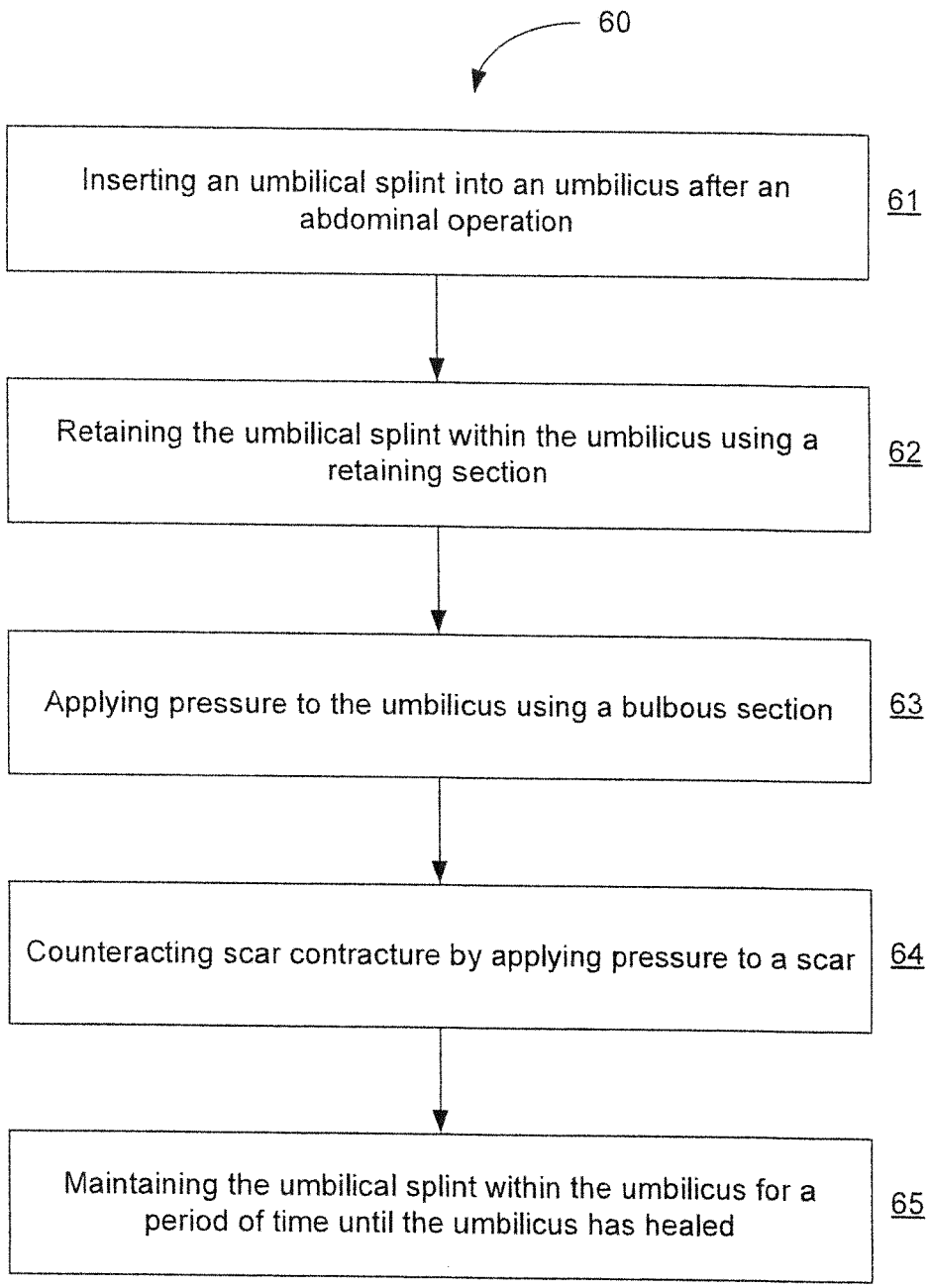
FIG. 6 shows a flow chart of a method for using an umbilical splint in accordance with an embodiment of the present invention.

A flow chart illustrating a method 60 of using an umbilical splint 10 is now shown in FIG. 6. In Block 61, the umbilical splint 10 is inserted into an umbilicus 3 after an abdominal operation. As described in reference to FIG. 1, the umbilical splint comprises an insertion portion 20 extending in a longitudinal direction LD and terminating at an insertion end 22.

Next, in Block 62, the umbilical splint 10 is retained within the umbilicus 3 using a retaining section 26 to engage the umbilicus 3. For example, the retaining section 26 may engage a lip 7 of the umbilical opening 5 to impede any withdrawal or expunging force acting on the umbilical splint 10.

Once inserted into the umbilicus 3, in Block 63, the umbilical splint 10 applies pressure to the umbilicus 3 using a bulbous section 24 of the insertion portion 20 to shape the umbilicus 3 after the abdominal operation. In a preferred embodiment, as seen in Block 64, the bulbous section 24 of the umbilical splint 10 counteracts scar contracture of the umbilicus 3 by applying pressure to a scar.

Finally, in Block 65, the umbilical splint 10 is maintained within the umbilicus 3 for a period of time until the umbilicus 3 has healed from the abdominal operation. While lengths will vary by patient 2, different approaches may be used.

In a preferred embodiment, a patient 2 may use the umbilical splint 10 continuously. The umbilical splint 10 may be removed for personal hygiene purposes such as cleaning the umbilicus 3, applying medication to the umbilicus 3 or scar, applying an application layer 50 to the insertion portion 20 of the umbilical splint 10 and/or washing the umbilical splint 10. Otherwise, the umbilical splint 10 may be retained within the umbilicus 3 until the umbilicus 3 has healed.

In another preferred embodiment, the patient 2 may use multiple umbilical splints 10 during the healing process. For example, the patient 2 may begin with a first umbilical splint 10 having a relatively small bulbous section 24. The bulbous section 24 is configured with a first bulbous circumference. Subsequently, as the umbilicus 3 of the patient 2 heals, the patient 2 may progress to one or more larger umbilical splints 10 having progressively larger bulbous sections 24 (and corresponding larger bulbous circumferences). In this manner, the umbilical splint 10 will continue to apply pressure to the umbilicus 3 as the umbilicus 3 heals and may allow the umbilical splint 10 to progressively shape the umbilicus 3 after an abdominal operation.

In other embodiments, the patient 2 may use or begin to use the umbilical splint 10 for repeated brief periods of time. For example, a patient 2 may use the umbilical splint three times a day for 20 minute intervals. In other embodiments, a patient 2 may insert the umbilical splint 2 for longer periods of hours, days or weeks. Furthermore, different regimens may be used to steadily increase the period of time the umbilical splint 10 is worn by the patient 2. The patient 2 may continue to use the umbilical splint 10 until the umbilicus 3 has healed from the abdominal operation or the chance of scar contracture is reduced or no longer present.

Although the insertion portion 20 of the umbilical splint 10 has been illustrated in FIGS. 1 to 5 as being round such that its bulbous circumference and retaining circumference have a substantially circular cross-section, it should be understood that other shapes, sizes and perimeters for the insertion portion 20 are possible. For example, as illustrated in FIGS. 7A to 7D and FIGS. 8A to 8D, the insertion portion 20 of umbilical splint 10 is shaped such that its bulbous circumference and retaining circumference are substantially ovular or non-circular, with different major and minor axes.

In some embodiments, the inventors have appreciated that bulbous and retaining circumferences having an oval or ovular shape are better retained within the umbilicus 3 compared to circular bulbous, retaining and/or opening circumferences. Furthermore, an ovular insertion portion 20 may result in a more pleasing umbilicus 3, once the umbilicus 3 has healed.

In other embodiments, the bulbous, retaining and/or opening circumferences may be asymmetric and/or different shapes from each other. For example, in one embodiment, the bulbous circumference may be an asymmetric shape, or even free-form, and the retaining circumference may be ovular. It should be understood that other shapes and configurations for the insertion portion 20 are possible and that the bulbous circumference, retaining circumference and opening circumference are not limited to the shapes described herein.

Figure 7A:
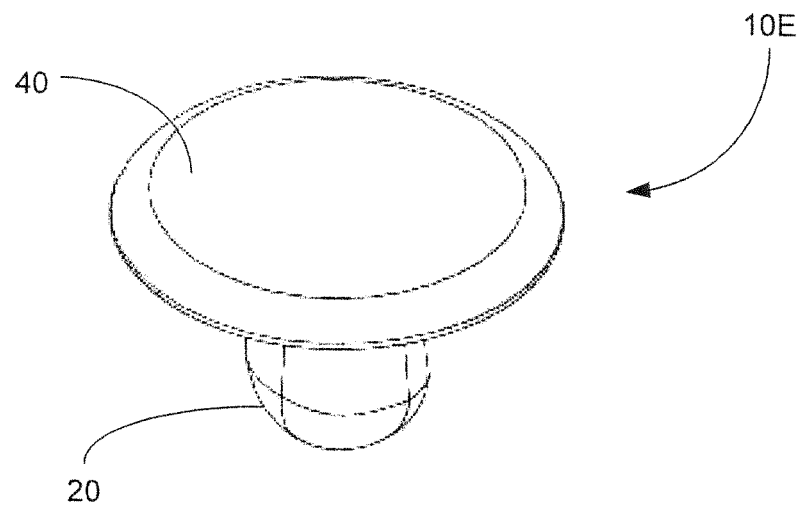
FIG. 7A shows a perspective view of an umbilical splint having an ovular insertion portion in accordance with an embodiment of the present invention.
Figure 7B:
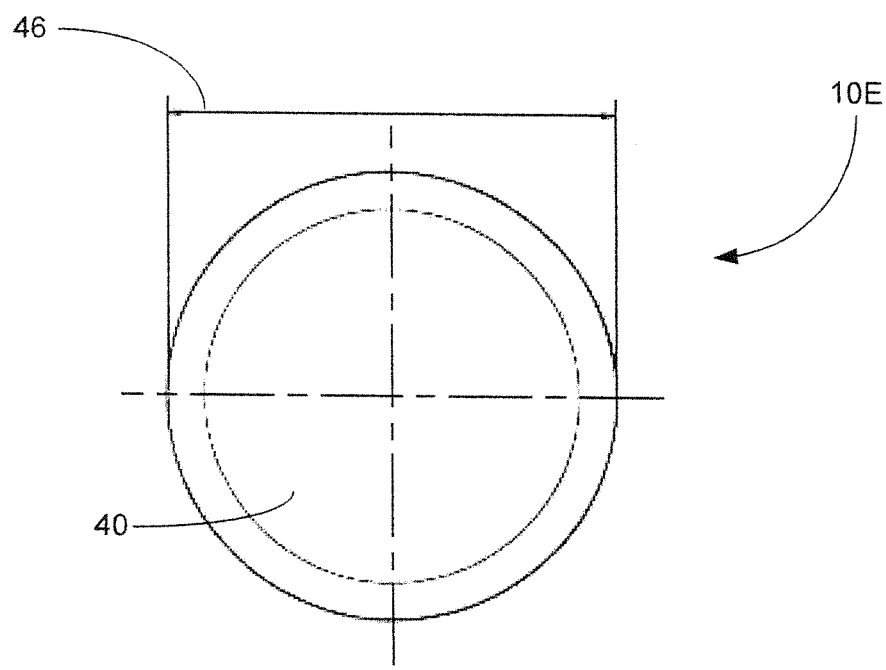
FIG. 7B shows a top view of the umbilical splint seen in FIG. 7A.

Referring now to FIGS. 7A to 7D, an umbilical splint 10E having an insertion portion 20 with an ovular opening circumference or cross-section is shown. Many features of umbilical splint 10 are similar to those previously described, such as the flange length 48 and insertion length 36. In FIG. 7B, a top view of the umbilical splint 10E illustrates a circular external flange 40. However, as previously mentioned, other shapes for the external flange 40 are also possible.

Figure 7C:
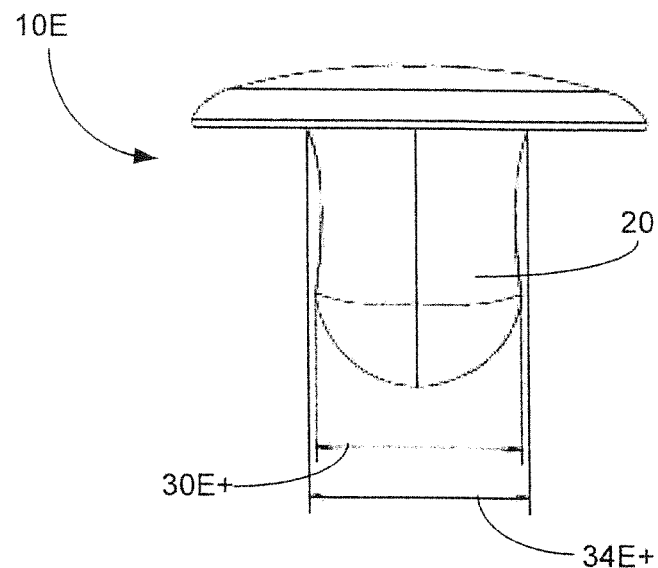
FIG. 7C shows a front view of the umbilical splint seen in FIG. 7A.
Figure 7D:
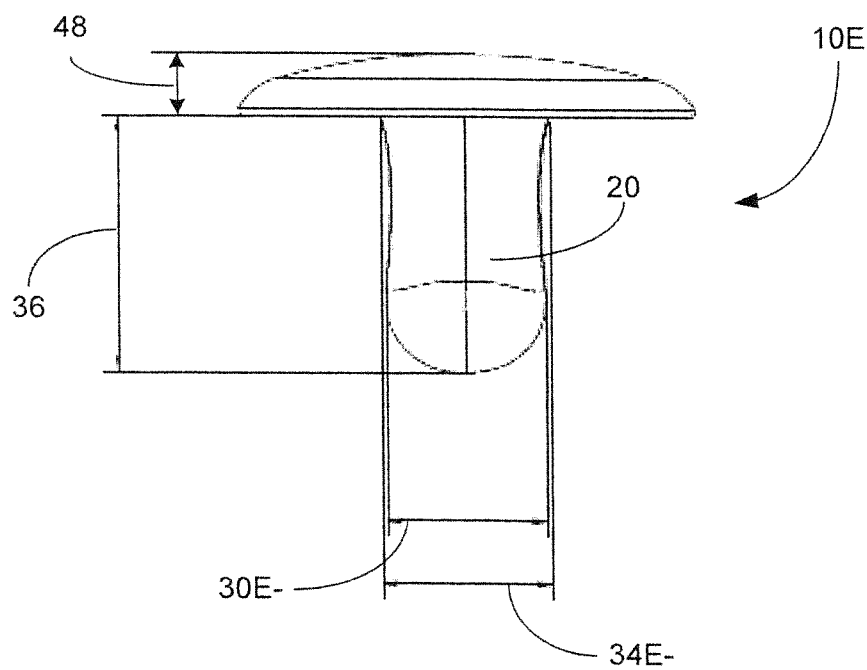
FIG. 7D shows a side profile view of the umbilical splint seen in FIG. 7A.

Referring to FIG. 7A, the umbilical splint 10E having an ovular insertion portion 20 is configured with an ovular bulbous circumference and an ovular opening circumference. As seen in FIG. 7C and FIG. 7D in front and side profile view, with the major axes (+) larger than the minor axes (−), such that each of the bulbous diameters 30E+, 30E− and opening diameters 34E+, 34E− are different from front-to-back and side-to-side. As shown in FIG. 7C, a front view of the umbilical splint 10E is shown with a major bulbous diameter 30E+ and a major opening diameter 34E+. In comparison to the side profile view in FIG. 7D, the major bulbous diameter 30E+ and the major opening diameter 34E+, seen in FIG. 7C, are larger than the minor bulbous diameter 30E− and the minor opening diameter 34E−, respectively. Such an ovular insertion portion 20 may provide a better distribution of pressure to the umbilical tissue 4 when placed inside the umbilicus 3. Furthermore, the shape may allow the umbilical splint 10E to stay retained within the umbilicus 3 unaided. Different shapes may also provide improved comfort for patients 2 than insertion portions 20 having circular or ovular shapes.

Figure 8A:
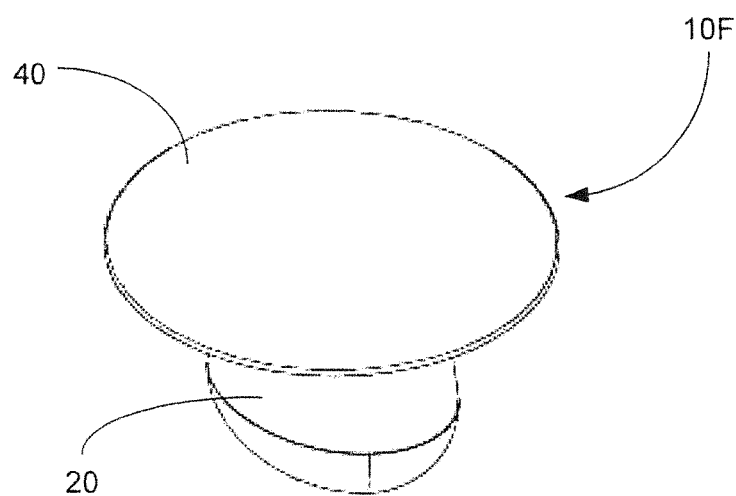
FIG. 8A shows a perspective view of an umbilical splint having an ovular insertion portion in accordance with an embodiment of the present invention.
Figure 8B:
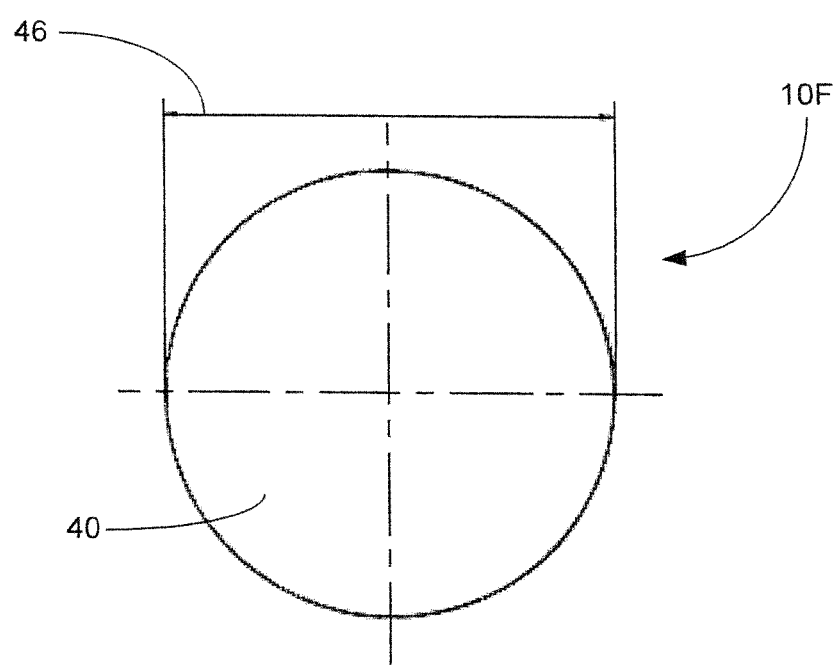
FIG. 8B shows a top view of the umbilical splint seen in FIG. 8A.
Figure 8C:
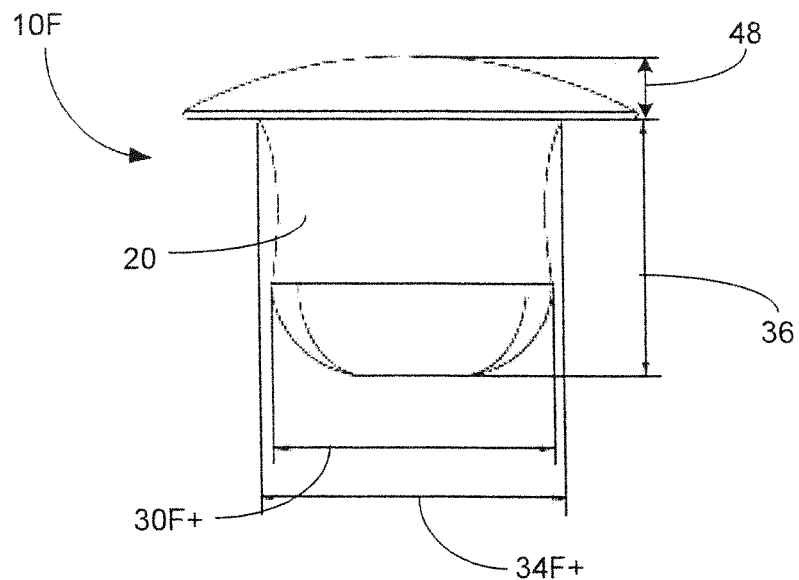
FIG. 8C shows a front view of the umbilical splint seen in FIG. 8A.
Figure 8D:
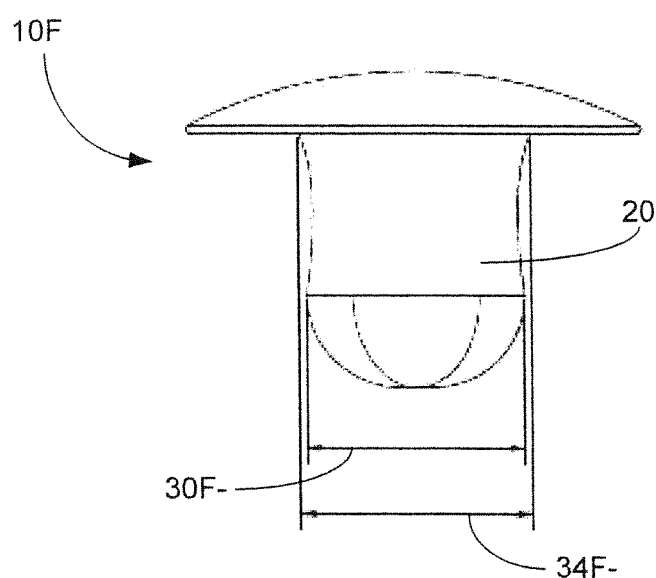
FIG. 8D shows a side profile view of the umbilical splint seen in FIG. 8A.

A similar relationship can be seen in the umbilical splint 10F shown in FIGS. 8A to 8D. The major bulbous diameter 30F+, seen in front view in FIG. 8C, is larger than the minor bulbous diameter 30F−, seen in side profile view in FIG. 8D. Similarly, the major opening diameter 34F+, seen in front view in FIG. 8C, is larger than the minor opening diameter 34F−, seen in side profile view in FIG. 8D. A similar relationship may exist with the retaining circumference having different side-to-side and front-to-back retaining diameters (not shown).

Finally, it should be understood that while the umbilical splints 10 and 10A to 10F have been described with respect to specific shapes, other shapes are also possible. Furthermore, the umbilical splints 10 and 10A to 10F, as described herein, may be constructed in different sizes for different sized patients 2, from infants and small children to adults.

Although this disclosure has described and illustrated certain preferred embodiments of the invention, it is also to be understood that the invention is not restricted to these particular embodiments rather, the invention includes all embodiments which are functional, or mechanical equivalents of the specific embodiments and features that have been described and illustrated herein. Similarly, the scope of the claims should not be limited by the preferred embodiments set forth in the examples, but should be given the broadest interpretation consistent with the description as a whole.

It will be understood that, although various features of the invention have been described with respect to one or another of the embodiments of the invention, the various features and embodiments of the invention may be combined or used in conjunction with other features and embodiments of the invention as described and illustrated herein.

The invention claimed is:

1. A method of post-operative care comprising:
   inserting an umbilical splint into an umbilicus after an abdominal operation, the umbilical splint comprising an insertion portion extending in a longitudinal direction and terminating at an insertion end;
   retaining the umbilical splint within the umbilicus using a retaining section of the insertion portion to engage the umbilicus;
   applying pressure to the umbilicus using a bulbous section of the insertion portion to shape the umbilicus after the abdominal operation; and
   maintaining the umbilical splint within the umbilicus for a period of time until the umbilicus has healed from the abdominal operation.

2. The method of post-operative care as claimed in claim 1, wherein the umbilical splint is used to counteract scar contracture of the umbilicus by applying pressure to a scar.

3. The method of post-operative care as claimed in claim 1, wherein the umbilical splint further comprises:
   an external flange having a flange diameter coupled to the insertion portion;
   wherein the insertion portion comprises:
      a bulbous section having a bulbous circumference and a bulbous diameter; and
      a retaining section having a retaining circumference less than the bulbous circumference;
      wherein the bulbous section is disposed between the retaining section and the insertion end, and
      wherein the retaining section is configured to engage a lip of the umbilicus such that the insertion portion is retained within the umbilicus;
   wherein the flange diameter extends beyond the bulbous diameter;
   wherein the external flange comprises:
      an underside surface facing the insertion end of the insertion portion; and
      an exterior surface, opposite the underside surface, and
   wherein the external flange is adapted to extend beyond an umbilical opening over the abdominal tissue surrounding the umbilical opening.

4. The method of post-operative care as claimed in claim 3, wherein the underside surface of the external flange is substantially planar such that the underside surface is operable to lay against an abdominal surface surrounding the umbilicus.

5. The method of post-operative care as claimed in claim 3, wherein the exterior surface of the external flange is rounded.

6. The method of post-operative care as claimed in claim 1, wherein a ratio of the bulbous circumference to the retaining circumference is between 1.0 and 1.4.

7. The method of post-operative care as claimed in claim 3, wherein the bulbous circumference is substantially ovular in shape.

8. The method of post-operative care as claimed in claim 3 wherein the external flange is formed of a rigid material.

9. The method of post-operative care as claimed in claim 3, wherein the bulbous portion is formed of a material selected from the group consisting of hard plastic, glass, metal, medical ceramic, medical plastic.

10. The method of post-operative care as claimed in claim 3, wherein the flange diameter is at least 1.5 times greater than the bulbous diameter.

11. The method of post-operative care as claimed in claim 3, wherein the flange diameter is at least 1.75 times greater than the bulbous diameter.

12. The method of post-operative care as claimed in claim 1, wherein the longitudinal direction of the insertion end is normal to the underside surface of the external flange.

13. The method of post-operative care as claimed in claim 1, wherein the insertion end is substantially planar.

14. The method of post-operative care as claimed in claim 1, further comprising, before inserting the umbilical splint into the umbilicus after the abdominal operation, applying a medicament to the insertion portion of the umbilical splint.

15. The method of post-operative care as claimed in claim 1, further comprising, before inserting the umbilical splint into the umbilicus after the abdominal operation, applying a silicone gel sheet to the insertion portion of the umbilical splint.

16. The method of post-operative care as claimed in claim 1, wherein the insertion portion is formed of a rigid material.

17. The method of post-operative care as claimed in claim 1, wherein the umbilical splint is formed of a single piece.

18. The method of post-operative care as claimed in claim 17, wherein the umbilical splint is formed of a hard plastic.

19. The method of post-operative care as claimed in claim 1, wherein the insertion end is rounded.

20. The method of post-operative care as claimed in claim 19, wherein the insertion end is substantially hemispherical in shape.

* * * * *